United States Patent [19]

Glover

[11] Patent Number: 4,564,017
[45] Date of Patent: Jan. 14, 1986

[54] METHOD AND APPARATUS FOR RESPIRATION MONITORING WITH AN NMR SCANNER

[75] Inventor: Gary H. Glover, Waukesha, Wis.

[73] Assignee: General Electric Company, Milwaukee, Wis.

[21] Appl. No.: 673,688

[22] Filed: Nov. 21, 1984

[51] Int. Cl.$^4$ ............................................. A61B 5/05
[52] U.S. Cl. .................................. 128/653; 128/721; 324/300; 324/307
[58] Field of Search ..................... 128/653, 716, 721; 324/309, 307

[56] References Cited

U.S. PATENT DOCUMENTS

Re. 23,950 10/1960 Williams ............................... 324/307
2,955,252 2/1955 Bloch et al. ........................... 324/307
3,052,834 9/1962 Schuster ............................... 324/313
3,714,551 1/1973 Pajak et al. ........................... 324/313

Primary Examiner—Kyle L. Howell
Assistant Examiner—Ruth S. Smith
Attorney, Agent, or Firm—Alexander M. Gerasimow; Douglas E. Stoner

[57] ABSTRACT

A method for eliminating or reducing breathing artifacts due to motion-induced phase and amplitude errors in the phase-encoding dimension when using Fourier transform imaging methods, such as spin warp, utilizes a repetition time (TR) which is an odd multiple of one quarter of the breathing cycle. In the preferred embodiment, method and apparatus are provided for determining the breathing cycle by monitoring the integrated spin-echo signal magnitude spectrum as a function of time.

12 Claims, 8 Drawing Figures

METHOD AND APPARATUS FOR RESPIRATION MONITORING WITH AN NMR SCANNER

CROSS REFERENCE TO RELATED APPLICATION

This application is related to commonly assigned U.S. patent application Ser. No. 673,690, filed by H. C. Charles and G. H. Glover concurrently with the present application.

BACKGROUND OF THE INVENTION

This invention relates to nuclear magnetic resonance (NMR) methods and apparatus. More specifically, this invention relates to a method and apparatus for monitoring respiration rate with an NMR scanner.

Acquisition of diagnostically useful images of the upper torso and abdomen utilizing NMR techniques is often complicated by motion-induced artifacts. The primary cause of motion is patient breathing. The source of these artifacts has been determined to be motion-induced phase and amplitude errors in the phase-encoding dimension when using Fourier transform imaging techniques, such as the one commonly referred to as "spin-warp." Numerous approaches have been suggested for minimization of these artifacts. Among the approaches suggested are breath holding, various gating schemes which involve data acquisition during expiration/inspiration, or controlled shallow breathing. However, all of these techniques involve either patient cooperation or increased scan time based on the full breathing cycle. Specific drawbacks associated with the proposed conventional techniques are, for example, that respiratory gating requires additional equipment to generate the gating signals and generally prolongs the imaging time. Breath holding and shallow breathing may work well with the volunteers, but are difficult or impossible for seriously ill or incapacitated patients who are the most likely subjects for NMR imaging.

It is, therefore, a principal object of the invention to provide a method for the reduction or elimination of motion-induced artifacts by non-gated synchrony with the breathing cycle, while eliminating the shortcomings of the afore-described conventional techniques.

SUMMARY OF THE INVENTION

A method is provided for reducing artifacts in NMR images due to motion-induced errors in the phase-encoding dimension when using Fourier transform imaging pulse sequences. In accordance with the method the breathing cycle of the subject to be scanned is determined and this information is then used to select a pulse sequence repetition time, TR, which is approximately an odd multiple of one quarter of the breathing cycle.

THe breathing period can be determined by any suitable manner, but in the preferred embodiment it is determined using scan data acquired with the NMR system by monitoring the integrated magnitude spectrum of the scan data as a function of time.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the acccompanying drawings in which:

DETAILED DESCRIPTION OF THE INVENTION

Figure 1:
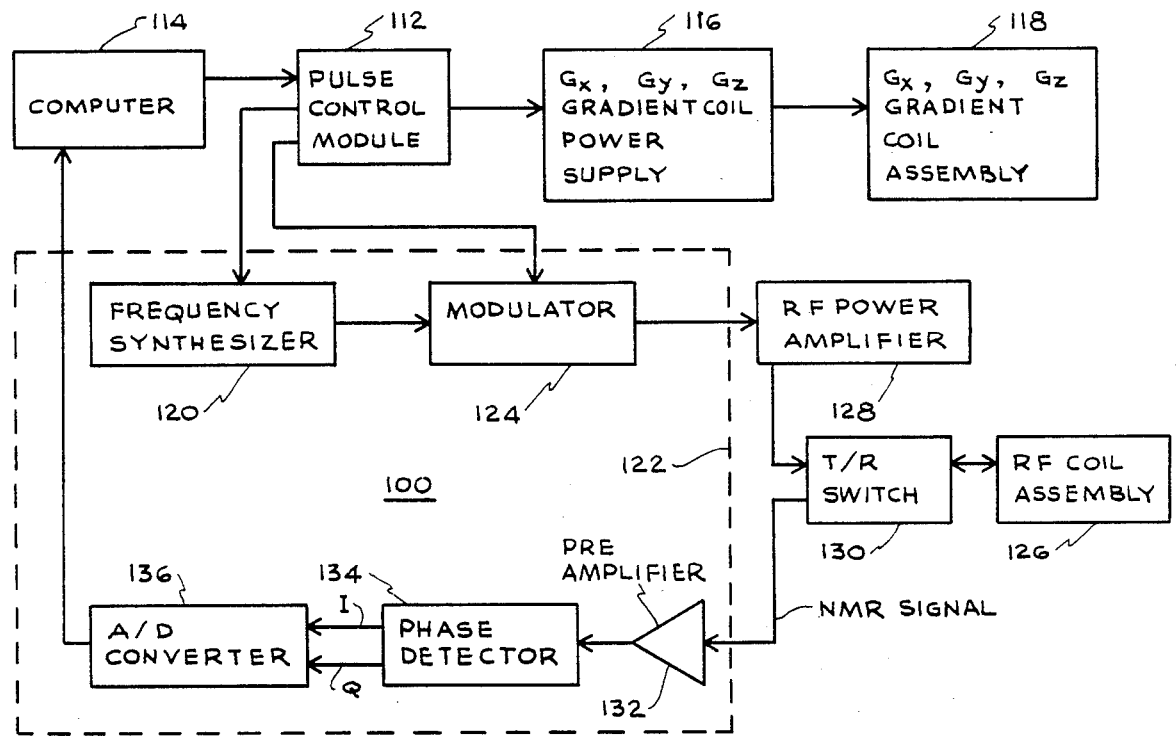
FIG. 1 depicts in block schematic form part of an NMR system useful for practicing the invention.

FIG. 1 is a block diagram of an NMR imaging system with respect to which the invention will be disclosed. The system, generally designated 100, includes a pulse-control module 112 which provides properly timed pulse signals under the control of a host computer 114 to gradient magnetic field power supplies, collectively designated 116, used to energize gradient coils which form part of a gradient coil assembly generally indicated by a block 118. The assembly contains coils which, when energized, produce the $G_x$, $G_y$, and $G_z$ magnetic field gradients directed in the x-, y-, and z-axis directions, respectively, of the Cartesian coordinate system. The use of the $G_x$, $G_y$, and $G_z$ gradients in imaging will be described hereinafter with reference to FIGS. 2 and 3.

Continuing with reference to FIG. 1, the pulse control module provides activating pulses to a radio frequency (RF) synthesizer 120 which is part of an RF transceiver system, portions of which are enclosed by dashed line block 122. The pulse control module also supplies modulating signals to a modulator 124 in the transceiver which modulates the output of the RF frequency synthesizer. The modulated RF signals are applied to an RF coil assembly 126 through an RF power amplifier 128 and a transmit/receive switch 130. The RF signals are used to excite nuclear spins in a sample object undergoing examination and which is positioned in the field of the RF coil.

The NMR signals from the excited nuclear spins are received by the same or a different radio-frequency coil as was used to excite nuclear spins. The received signals are applied through the transmit/receive switch to an RF preamplifier 132 and then to a quadrature phase detector 134 which provides in phase and quadrature outputs I and Q, respectively. The detected signals are digitized by A/D converter 136 and applied to computer 114 for processing in a well-known manner to, for example, reconstruct NMR images of the sample object.

Figure 2:
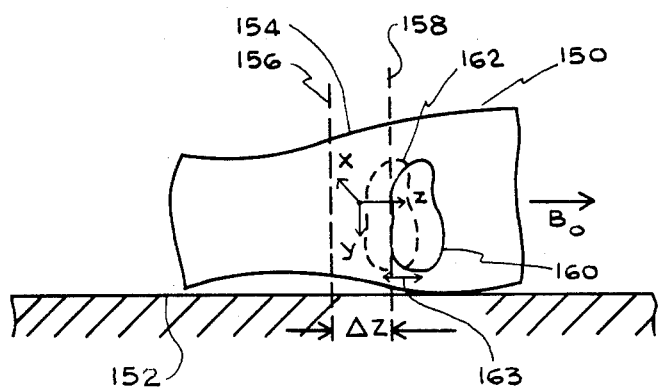
FIG. 2 depicts a portion of a supine patient including an imaging slice selected by the process of selective excitation.

The NMR pulse sequences utilized with the invention will be best understood if initial reference is made to FIG. 2 which depicts an NMR sample object 150, which in this case is a partially illustrated supine patient resting on a patient table 152. The patient typically is positioned in and longitudinally aligned with a polarizing magnetic field $B_o$ directed in a positive Z-axis direction of the coordinate system. The origin of the coordinate system is typically taken to be the center of an imaging slice 154 having a thickness $\Delta Z$ defined by dash lines 156 and 158. The thickness and the position of the slice which, in this case, is selected to be in the region of the upper-third torso of patient 150, is determined by the strength of the polarizing magnetic field $B_o$, the magnitude of the gradient magnetic fields used, and the frequency content used to modulate the RF excitation pulses, as is well known to those skilled in the art.

Figure 3:
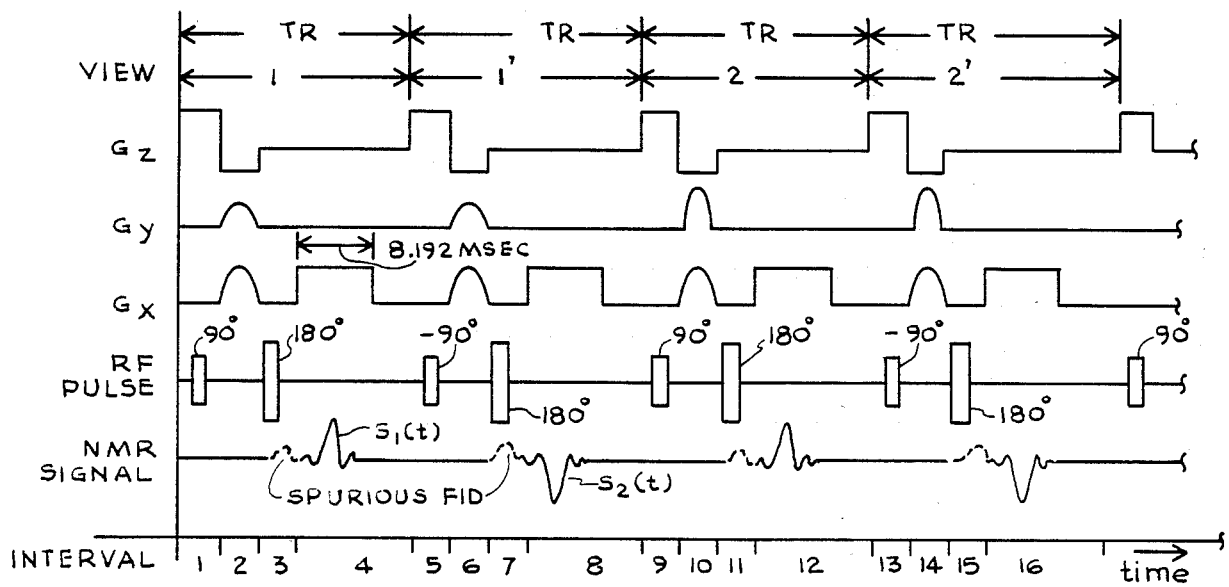
FIG. 3 depicts an exemplary embodiment of a spin-warp pulse sequence which may be utilized in practicing the invention.

Reference is now made to FIG. 3 which depicts a portion of what now can be referred to as a conventional imaging pulse sequence of the type known as two-dimensional Fourier transform (2DFT) and which is frequently also referred to as "spin warp." This pulse sequence is useful in obtaining, in a well-known manner, imaging data to reconstruct an image of, for example, imaging volume 154 depicted in FIG. 2. This pulse sequence is an improvement over conventional pulse sequences in that it utilizes phase-alternated RF excitation pulses which, as disclosed and claimed in U.S. Pat. No. 4,443,760 (assigned to the same assignee as the present invention and incorporated herein by reference), produce phase-alternated NMR signals. When these signals are subtracted, those signal components having an inverted phase reinforce while undesired base-line error components whose phase was not reversed cancel.

A more detailed description of the spin-warp imaging pulse sequence will now be undertaken with reference to FIG. 3 which depicts four phase-encoding views 1, 1', 2, and 2'. Each of view pairs 1-1' and 2-2' utilize the same amplitude of the $G_y$ phase-encoding gradient which will be discussed hereinafter. In practice, the $G_y$ gradient can be selected to have, for example, 128, 256, or 512 different amplitudes. Referring now to view 1 in FIG. 3, there is shown an interval 1 (indicated along the horizontal axis), a selective 90° RF excitation pulse applied in the presence of a positive $G_z$ magnetic field gradient pulse. Pulse control module 112, FIG. 1, provides the needed control signals to the frequency synthesizer and modulator so that the resulting excitation pulse is of the correct frequency and properly modulated to excite nuclear spins only in imaging slice 154 depicted in FIG. 2. Typically, the excitation pulse can be amplitude modulated by a sin x/x function such that the excited imaging slice has a substantially rectangular profile. The frequency of the excitation pulse is dependent on the strength of the applied magnetic fields and the NMR species being imaged in accordance with the well-known Larmor equation. The pulse-control module also applies activating signals to the gradient power supply to generate, in this case, the $G_z$ gradient pulse.

Continuing with reference to FIG. 3, $G_z$, $G_y$, and $G_x$ gradient pulses are applied simultaneously in interval 2. The $G_z$ gradient in interval 2 is a rephasing pulse typically selected such that the time integral of the $G_z$ gradient waveform over interval 2 is approximately equal to a negative $\frac{1}{2}$ of the time integral of the $G_z$ gradient waveform over interval 1. The function of this $G_z$ pulse is to rephase the nuclear spins excited in interval 1. The $G_y$ gradient pulse, as alluded to hereinabove, is a phase-encoding pulse selected to have different amplitudes in each of views 1, 2, etc., to encode spatial phase information in the y-axis direction.

The $G_x$ gradient pulse in interval 2 is a dephasing pulse needed to dephase the nuclear spins by a predetermined amount to delay the time of occurrence of a spin-echo signal $S_1(t)$ in interval 4. The spin echo is produced by the application of a typically, nonselective 180° RF pulse in interval 3. As is known, the 180° RF pulse is a time-reversal pulse which reverses the direction of spin dephasing. This in combination with the linear $G_x$ magnetic field gradient pulse results in a spin-echo signal being produced in interval 4. This spin-echo signal is sampled in the presence of the linear $G_x$ gradient pulse to encode spatial information in the direction of the X axis.

View 1' is substantially identical to view 1 with the exception that the 90° RF pulse applied in interval 5 is 180° out of phase relative to the 90° pulse in interval 1, as suggested by the negative sign. The same relationship exists between views 2-2', 3-3', . . . , etc. As a result of the phase alternation, the $S_2(t)$ spin-echo signal in interval 8 is also phase alternated relative to spin-echo signal $S_1(t)$. However, the spurious FID signals due to imperfect 180° RF pulses preceding the spin-echo signals are not phase alternated. In this manner, if signal $S_2(t)$ is subtracted from signal $S_1(t)$, the spin-echo signals reinforce, while the undesired spurious FID signals, along with other error components, such as DC offset, cancel. However, as a result of repeating each view with the phase of the 90° RF pulse inverted, the total scanning time is doubled.

In view 2, interval 6, the amplitude of the $G_y$ gradient is incremented to its next value and repeated in view 2', interval 16. This process is repeated until the $G_y$ gradient is sequenced through its entire range of amplitudes. At the completion of the scan process, image information is obtained by applying a two-dimensional Fourier transform process to the collected data.

An additional feature to be noted with reference to FIG. 3 is that the 90° RF pulses occur at time intervals having a length of TR. Interval TR is termed the repetition time and is defined as the period of time between the beginning of a pulse sequence (one view) and the beginning of a succeeding, substantially identical, pulse sequence. By properly adjusting the repetition time, it is possible to introduce a $T_1$ dependence into the spin-echo signals from which $T_1$-weighted images can be reconstructed.

As will become apparent hereinafter, judicious choice of the repetition time can be used to significantly reduce or eliminate breathing motion artifacts. It has been determined that these artifacts are caused by motion-induced phase and amplitude errors in the phase-encoding direction (Y axis in the case of the pulse sequence depicted in FIG. 3) when using the spin-warp imaging sequence. The artifacts due to such errors should be distinguished from image blurring (loss of resolution) due to simple displacement of pixel information from its true position in the image. Rather, the artifacts which are reduced or eliminated by the method of the invention are actual ghost images (artifacts) of the real (desired) image which are displaced in the phase-encoding direction. The displacement of the ghost images is due to the fact that the scan data, which represents the Fourier transform of the object, is distorted. In this case, phase errors actually represent a shift in pixel position in K-space and thereby account for the displacement.

Figure 4:
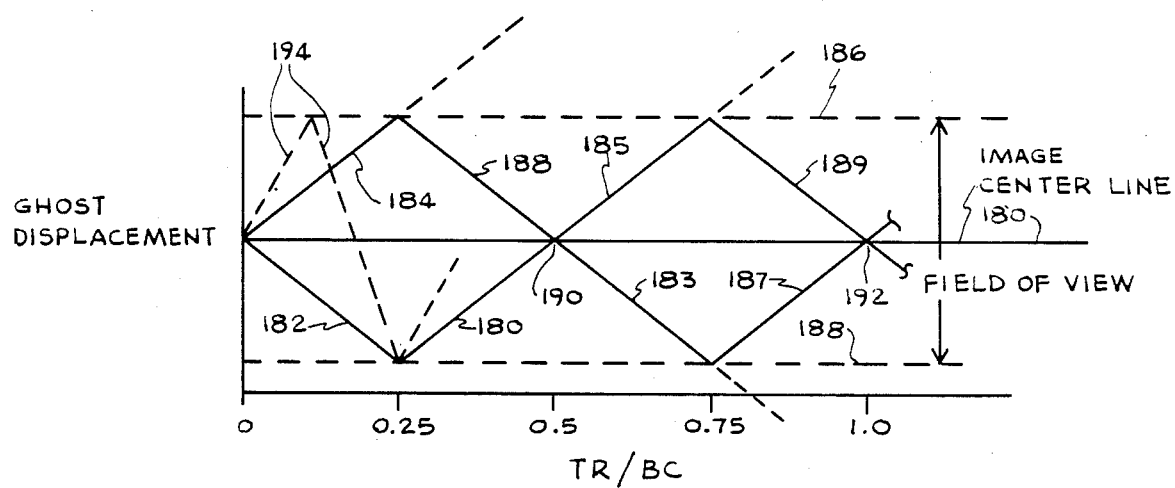
FIG. 4 depicts graphically ghost artifact displacement from the actual image versus the ratio of pulse sequence repetition time TR to the breathing rate BC where the number of averages is equal to 2.

It has been discovered by the Applicants herein that the spatial displacement of the artifacts from the actual position of the subject matter in the image is related to the ratio of the repetition time TR to the breathing cycle BC (TR/BC). This relationship is depicted in FIG. 4 in which the displacement of the artifacts from image center line 180 is indicated along the vertical axis, while the ratio TR/BC is indicated along the horizontal axis. It is apparent that this is in fact a linear relationship which is manifested as a repeating triangular relationship due to Nyquist folding in the phase-encoding (or virtual time) domain. The linearity of the relationship is apparent from line segments 182–185 which indicate ghost displacement from the image center line. The solid line portions represent ghost displacement within the system field of view, bounded by dash lines 186 and 188 disposed on either side of center line 180. In an idealized NMR system, displacement lines would continue beyond the field-of-view lines, as suggested by the dash line extensions of lines 182–185. In a practical system, however, due to sampling rate limitations, displacement lines 182–185 fold back into field of view as indicated by solid line segments 186–189, respectively. Because of this apparent periodic behavior, the use of TR=nBC/4, wherein n=1, 3, 5, . . . , etc., (i.e., TR=0.25BC, 0.75BC, 1.25BC, etc.), in a pulse sequence, such as that described with reference to FIG. 3, provides images in which the artifact image is displaced to the edge of the field of view and does not interfere with the desired image. This technique has been verified and found to have a reducing effect on the artifacts. In one example, images were acquired using an arbitrary repetition time TR=550 msec., and TR=833 msec. (TR=BC/4 selected in accordance with the invention. The image acquired with TR=550 msec. showed a motion-induced artifact overlapping the desired image. In the second case with TR=833 msec., the image had substantially minimized artifacts even when viewed with window and level settings (used to control image intensity parameters) set to enhance artifacts.

Although it appears that by selecting TR=0.5BC and 1BC, for example, (corresponding to the superposition of ghost images over the desired image, points 190 and 192 in FIG. 4) images could be produced which are artifact free, in practice this does not work well. The reasons are the lack of registration between the ghost and desired images and the additive effect of blurring artifacts in each image.

The required TR times, in accordance with the invention, for patient-breathing rates of 10 to 25 breaths per minute are in the range of 0.6–1.2 sec., corresponding to TR=1BC/4. Repetition times in this range are sufficiently short so as not to unduly extend data collection times and do not greatly degrade image contrast. In some cases, as with rapidly breathing patients, TR=3BC/4 may be advantageously utilized. This corresponds to TR=1.5–2.0 seconds. Repetition times corresponding to 5BC/4 and 7BC/4 represent TR values which are too long for patient studies, but which may be useful with laboratory animals which typically have naturally high respiration rates. If contrast suffers due to use of the inventive technique with partial saturation spin-echo techniques, then the alternative is to use other techniques known to those skilled in the art, such as saturation recovery and inversion recovery pulse sequences, to obtain $T_1$-weighted images.

It has been found that the effect of increasing the amplitude of breathing by a factor of 2 (using phantom displacement of 5 cm. and 10 cm.) resulted in enhancement of intensity in ghosts, as well as the appearance of higher-order ghosts, without change in the distance from the actual image to the first ghost image. Thus, the important parameter in terms of ghost displacement is the TR/BC ratio (FIG. 4). The breathing amplitude affects only the ghost intensity.

The displacement lines (182–185) in FIG. 4 represent the first order ghost image. There are in fact less intense higher-order ghosts which are also displaced from the center line in a manner similar to that described for the first-order ghosts with reference to FIG. 4, but with a shorter period as suggested by dash line 194 in FIG. 4. It should be noted that for the high-order ghost artifacts, the maximum displacement points coincide with those of the first-order ghosts at TR=nBC/4, as described hereinbefore. In this manner, the method of the invention is also effective in reducing or minimizing the effects of higher-order artifacts.

The determination of the breathing rate for the purpose of calculating optimum repetition times for eliminating or minimizing motion-induced artifacts may be accomplished by any suitable means such as conventional external respiration monitors. In the preferred embodiment of the invention, however, the NMR spectrometer instrument, itself, is utilized for this purpose. Briefly, this is accomplished by acquiring NMR data in such a manner that the breathing motion induces amplitude modulation of the NMR signal. Breathing rate can then be determined by analysis of the modulated signals. The manner in which this is realized will now be described in greater detail with initial reference to FIGS. 2 and 3.

The respiration rate can be determined by monitoring the integrated spin-echo magnitude spectrum as a function of time. To this end, a transaxial scan through the abdomen (such as slice 154, FIG. 2) using the pulse sequence of FIG. 3 with, for example, TR=200 msec., but without using the $G_y$ phase-encoding gradient, forms the data set. Phase-alternated views (1', 2' . . . etc.) are not counted toward the 64-view total, but are used to eliminate baseline errors, as discussed before. The 90° RF excitation pulses are modulated so as to excite an imaging slice 154 (FIG. 2) in the upper torso near, for example, the diaphragm, which is designated by reference numeral 160 in FIG. 2. As the patient breathes, the diaphragm (or other tissue mass), which normally lies outside the plane of the imaging slice, moves in and out of the volume of the slice, as suggested by the dash line depiction 162 of the diaphragm and bidirectional arrow 163. The intensity of the spin-echo signal originating from slice 154 changes with the breathing cycle due to the respiration-induced changes in the proton spin density and movement of material within the imaging slice being monitored.

Figure 5:
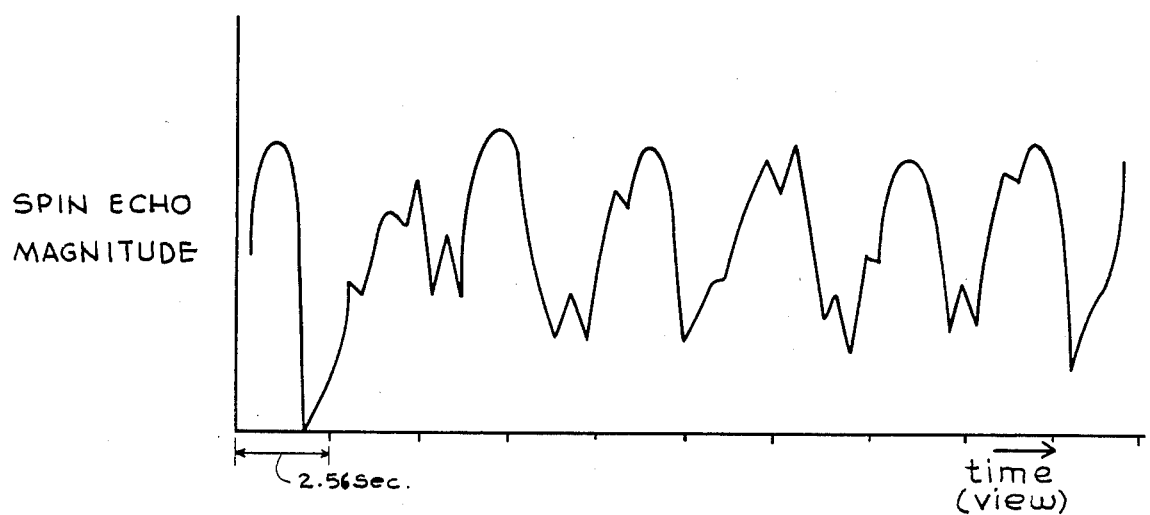
FIG. 5 is a plot depicting integrated spin-echo magnitude versus time from which the breathing rate information can be derived.

FIG. 5 depicts a plot of the complex spin-echo modulus (magnitude) of a data set acquired using a 64-view sequence described hereinabove integrated over the sampling interval over which the spin-echo signal is sampled. One example of such an interval, 8.192 msec. long, is interval 4 (FIG. 3), where the spin-echo signal is sampled a number of times equal to 128, 256, or 512. In FIG. 5, the magnitude of the spin echo is indicated along the vertical axis, while the horizontal axis corresponds to view number (1 to 64 in this case), or time with 2.56 sec./division. The repetition time TR for the pulse sequence was selected to be 200 msec., which, due to the use of phase-alternated pulses (views 1', 2', . . . , etc.) to eliminate baseline error components, results in a 400 msec. total period for views 1 and 1', 2 and 2', etc.

As is apparent in FIG. 5, the spin-echo magnitude has a cyclic character which has been found to be in accord with the respiratory cycle. The breathing period can be estimated by determining the average time between the magnitude peaks and recalling that there are 2.56 sec./division. In this manner, the breathing cycle is seen to be about 3.5 seconds.

Figure 6:
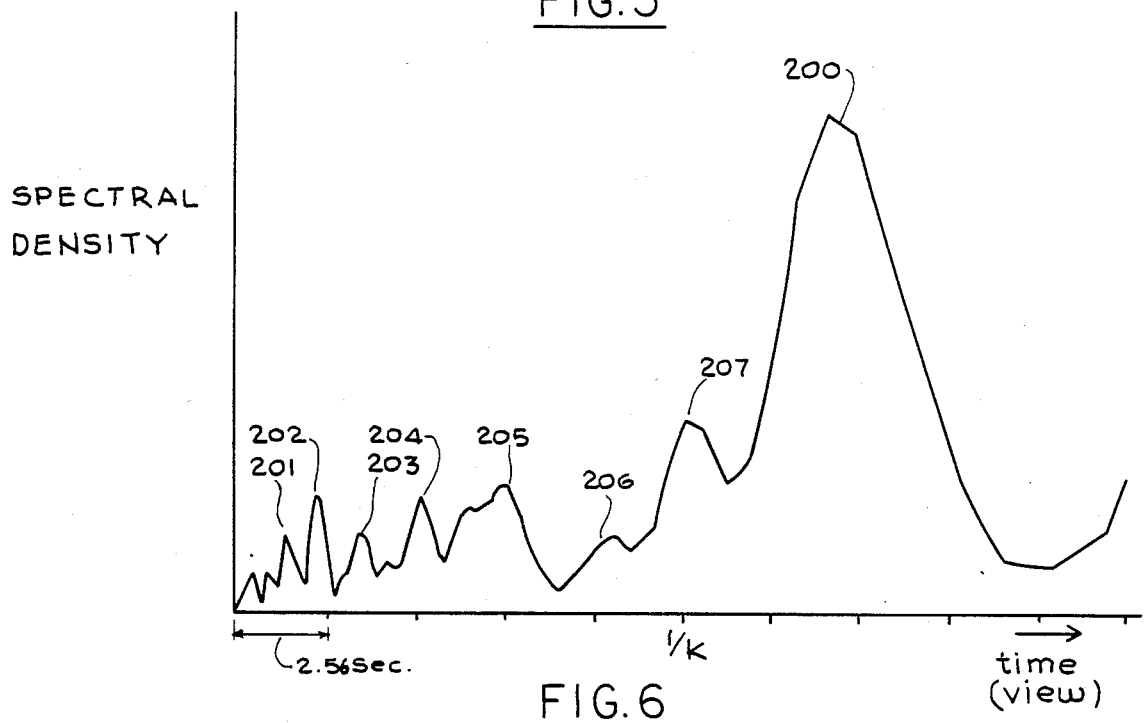
FIG. 6 is a plot depicting spin-echo spectral density versus respiration rate obtained by taking the Fourier transform of the spectral density depicted in FIG. 5.

A more precise method for measuring the breathing period is to plot the Fourier transform of the spin-echo modulus with respect to view (or time) as a function of respiration period (instead of the customary frequency abcissa). Such a plot is depicted in FIG. 6, which corresponds to the data in FIG. 5. A peak 200 in the spectrum occurs at approximately 3.75 seconds and is taken to be the respiration period. In general, to determine the breathing period, it is desired to locate the spectrum component having the maximum height at the lowest frequency. Advantageously, a peak-finder computer program can be used to analyze the spectral data to find the peak with the highest amplitude at the lowest frequency, thereby to determine the breathing cycle.

The smaller peaks, such as those designated 201–207 represent the spectra of complicated patient motion. It has been found that too many such peaks with large amplitudes indicate considerable patient motion. Experience has also shown that under such conditions, useable images are usually difficult to obtain. The presence and severity of such motion has been monitored and used as an indicator of whether satisfactory images could be obtained. It will be apparent that such an indication can be advantageously obtained in preliminary studies of the breathing cycle, without actually performing imaging scans. This permits a more efficient use of scanner time.

The detailed method of determining the breathing period described hereinabove may be best appreciated by considering a pulse sequence, such as that depicted in FIG. 3, wherein, for example, 64 spin-echo signals ($S_i(t)$, i=1, 2, ..., 64) are observed without application of a $G_y$ phase-encoding gradient. The spin-echo magnitude (spin-echo modulus, $M_i$) can be calculated according to the equation:

$$M_i = \sqrt{\int_o^{T_s} |S_i(t)|^2 \, dt} = \sqrt{\int_o^{T_s} [R(S_i)]^2 + [I(S_i)]^2 \, dt} \quad (1)$$

where $T_s$ is the duration a spin-echo signal is sampled (e.g., $T_s=8.192$ msec.), and $R(S_i)$ and $I(S_i)$ designate real and imaginary parts of the complex spin echo.

In discrete form, $M_i$ may be stated as $$M_i = \sqrt{\sum_{k=1}^{N_s} |E_i(t_k)|^2} = \sqrt{\sum_{k=1}^{N_s} R(S_i(t_k))^2 + I(S_i(t_k))^2} \quad (2)$$

where $E_i$ is the discrete spin-echo signal sample and $N_s$ is the number of samples taken in time $T_s$. This form of the expression is particularly appropriate because the scan data actually comprises discrete samples of the NMR spin-echo signals.

The Fourier transform (spectral density) of the echo modulus needed to obtain the plot of spectral density versus view or time is performed according to the following equation $$FFT(M_i) = F_K \quad (3)$$

where $K=1, \ldots, N$ views. The graph such as that in FIG. 6 is then obtained by plotting $F_K$ as the ordinate and $1/K$ as the abcissa.

Figure 7:
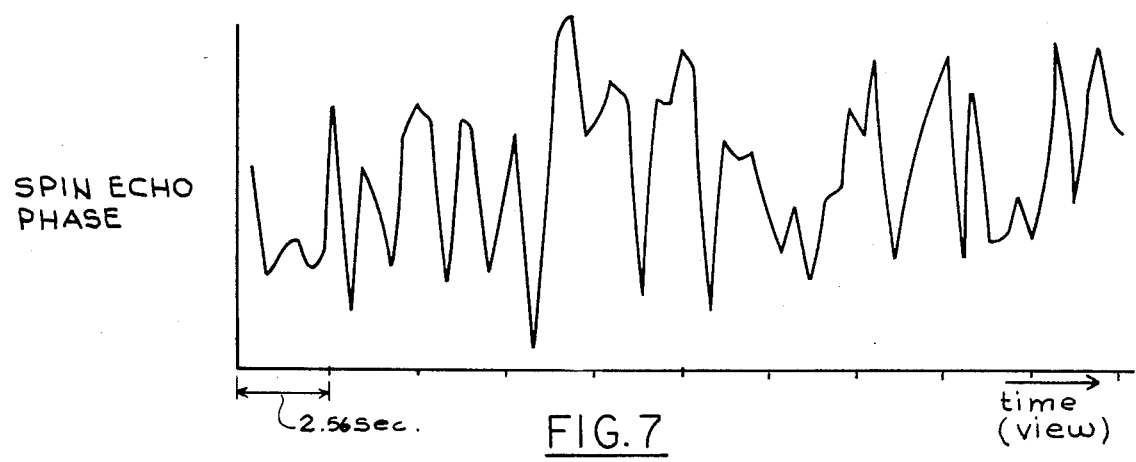
FIG. 7 is similar to FIG. 6, but depicts integrated spin-echo phase versus time.

An analysis has also been performed attempting to determine whether the phase of the complex spin echo integrated over the sample interval (8.192 sec.) could be used to determine the breathing period. A plot of phase versus view number is depicted in FIG. 7. It is seen that interpretation of the phase plot is not as easy as that of the magnitude, probably because the integral extended over the entire spin-echo time.

Analysis has also been performed of plots of the Fourier transform, which is in fact just the projection of the subject onto the readout axis. The plots were very similar to those in FIG. 5 when the integral contained the entire projection width. If only the FFT samples comprising the center 10 cm. of the projection were used, the amplitude of the excursions became greater as might be expected, but a significantly greater information content was not obtained.

In the preferred embodiment, the spin-echo modulus ($M_i$), and the Fourier transform of $M_i$, ($F_K$), are determined in computer 114, which is part of the NMR system described with reference to FIG. 1. It is, however, possible to utilize dedicated circuit devices to determine $M_i$ and $F_K$. An exemplary system which could be used will be described next with reference to FIG. 8.

Figure 8:
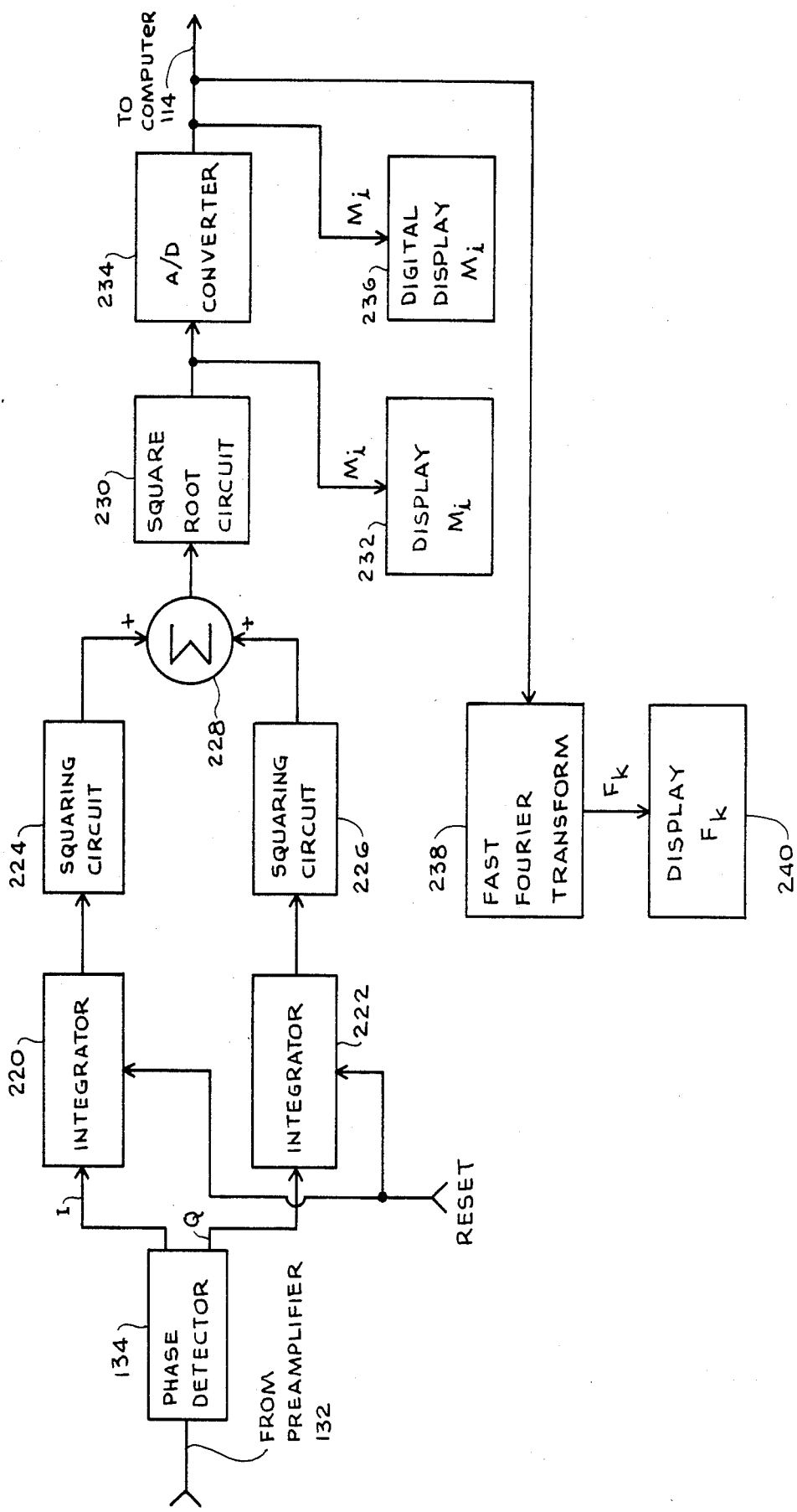
FIG. 8 depicts an exemplary system which could be used to determine the respiration period in accordance with the invention.

Referring now to FIG. 8, there is shown a quadrature phase detector 134 coupled at its input to receive NMR signals from a preamplifier 132. Both the detector and preamplifier may be the same devices 134 and 132 as in the system of FIG. 1. Quadrature outputs I and Q are each applied to real time, analog integrator circuits 220 and 222. The function of integrators 220 and 222 is to integrate, over interval $T_s$ ($T_s=8.192$ msec.), the NMR signals sampled during each view of a pulse sequence. To this end, upon completion of the integration operation for one view, the integrators are reset (e.g., by a reset signal from pulse control module 112, FIG. 1) in anticipation of the integration operation for the next view. The outputs of the integrator circuits are squared in circuits 224 and 226, summed in a summer circuit 228. The square root of the resulting sum signal is taken by a square root circuit 230.

It will be recognized that the above-described operation determines the value of spin-echo modulus $M_i$ in accordance with Equation (1). The spin-echo modulus can be displayed on a monitor 232 coupled to square root circuit 230. The display, which would be similar to that plot displayed in FIG. 5, could then be used to estimate the breathing period in the manner described hereinabove. It should be noted that elimination of the step of taking the square root of the signal would not materially alter the use of the plot for estimating the breathing period. The effect would be to alter the amplitude of the peaks displayed in FIG. 5, but not the temporal positions thereof.

The output of square root circuit 230 is digitized in A/D converter 234, and applied to digital display 236, FFT unit 238, and, optionally, to computer 114. The plot displayed on display 236 is similar to that depicted in FIG. 5 and can be used for the same purpose. The digitized signals are sampled and stored in FFT unit 238 which calculates $F_K$, the Fourier transform, of the spin-echo modulus in accordance with Equation (3). A display 240 coupled to the FFT unit is used to display $F_K$ as the ordinate and $1/K$ as the abscissa, in the manner described hereinabove with reference to FIG. 6. It should be noted that computer 114 could be used, instead of separate FFT unit 238, to perform the transform operation.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. A method of determining the respiration period of a patient using scan data obtained with an NMR scanner, said method comprising the steps of:
   acquiring amplitude-modulated NMR scan data of a predetermined region of the patient; and
   analyzing said scan data to derive the respiration rate of the patient.

2. The method of claim 1 wherein said step of acquiring comprises scanning the patient with a Fourier transform pulse sequence having a plurality of views, and wherein the scan data comprises spin-echo signals acquired in the absence of phase-encoding variable amplitude magnetic field gradient pulses.

3. The method of claim 2 wherein said step of analyzing comprises:
   determining the spin-echo modulus, $M_i$, to ascertain the cyclic character thereof and estimating therefrom the respiration period.

4. The method of claim 3 wherein the spin-echo modulus is determined using equation $$M_i = \sqrt{\int_0^{T_s} [R(S_i)]^2 + [I(S_i)]^2 \, dt}$$

where $T_s$ is the spin-echo sampling rate and $R(S_i)$ and $I(S_i)$ designate real and imaginary parts of the complex spin echo.

5. The method of claim 3 wherein the spin-echo modulus is determined using equation $$M_i = \sqrt{\sum_{k=1}^{N_s} [R(S_i(t_k))]^2 + [I(S_i(t_k))]^2}$$

where $N_s$ is the number of times each spin-echo signal is sampled and $R(S_i(t_k))$ and $I(S_i(t_k))$ designate real and imaginary parts of the complex spin echo.

6. The method of claim 2 wherein said step of analyzing comprises:
   determining the spin-echo modulus, $M_i$;
   taking the Fourier transform of $M_i$ with respect to time to determine the spectral density ($F_K$) of $M_i$; and
   identifying a spectrum component having maximum magnitude at the lowest frequency, wherein the time of occurrence of said spectrum component is taken as the respiration period.

7. The method of claim 6 wherein the spin-echo modulus is determined using equations $$M_i = \sqrt{\int_0^{T_s} [R(S_i)]^2 + [I(S_i)]^2 \, dt}$$

where $T_s$ is the spin-echo sampling duration and $R(S_i)$ and $I(S_i)$ designate real and imaginary parts of the complex spin echo.

8. The method of claim 6 wherein the spin-echo modulus is determined using equation $$M_i = \sqrt{\sum_{k=1}^{N_s} R(S_i(t_k))^2 + I(S_i(t_k))^2}$$

where $N_s$ is the number of times each spin-echo signal is sampled and $R(S_i(t_k))$ and $I(S_i(t_k))$ designate real and imaginary parts of the complex spin echo.

9. Apparatus for determining the respiration period of a patient using scan data obtained with an NMR scanner, said apparatus comprising:
   means for acquiring amplitude-modulated NMR scan data of a predetermined region of the patient; and
   means for analyzing said scan data to derive the respiration rate of the patient.

10. The apparatus of claim 9 wherein said means for acquiring comprises means for scanning the patient with a Fourier transform pulse sequence having a plurality of views, and wherein the scan data comprises spin-echo signals acquired in the abscence of phase-encoding variable amplitude magnetic field gradient pulses.

11. The apparatus of claim 10 wherein said means for analyzing comprises:
   means for determining the spin-echo modulus, $M_i$, to ascertain the cyclic character thereof and estimating therefrom the respiration period.

12. The apparatus of claim 10 wherein said means for analyzing comprises:
   means for determining the spin-echo modulus, $M_i$;
   means for taking the Fourier transform of $M_i$ with respect to time to determine the spectral density ($F_K$) of $M_i$; and
   means for identifying a spectrum component having maximum magnitude at the lowest frequency, wherein the time of occurrence of said spectrum component is taken as the respiration period.

* * * * *

UNITED STATES PATENT AND TRADEMARK OFFICE
CERTIFICATE OF CORRECTION

PATENT NO. : 4,564,017
DATED : January 14, 1986
INVENTOR(S) : Gary H. Glover

It is certified that error appears in the above-identified patent and that said Letters Patent is hereby corrected as shown below:

Column 5, line 34, after the numeral "4" insert -- ) --.
Column 7, line 17, change "in" to --In--.
Column 7, line 45 (Equation 1) that portion of the equation reading $$T_o^s \quad \text{should read} \quad \int_o^{T_s} \quad \text{BOTH OCCURRENCES}$$

Column 9, line 40 (in equation) that portion of the equation reading $$T_o^s \quad \text{should read} \quad \int_o^{T_s}$$

Column 10, line 12 (in equation) that portion of the equation reading $$T_o^s \quad \text{should read} \quad \int_o^{T_s}$$

Column 10, line 41, change "abscence" to --absence--.

Signed and Sealed this

Twenty-fifth Day of November, 1986

*Attest:*

DONALD J. QUIGG

*Attesting Officer*   *Commissioner of Patents and Trademarks*